(12) United States Patent
Nissilä

(10) Patent No.: US 6,775,566 B2
(45) Date of Patent: Aug. 10, 2004

(54) ELECTRODE STRUCTURE AND HEART RATE MEASURING ARRANGEMENT

(75) Inventor: Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/952,046

(22) Filed: Sep. 13, 2001

(65) Prior Publication Data

US 2002/0082491 A1 Jun. 27, 2002

(30) Foreign Application Priority Data

Oct. 18, 2000 (FI) ............................................. 20002304

(51) Int. Cl.$^7$ ............................................. A61B 5/0408
(52) U.S. Cl. ..................... 600/382; 600/386; 600/391; 600/393; 600/509
(58) Field of Search ....................... 600/382, 390–393, 600/386, 503, 509; 128/903

(56) References Cited

U.S. PATENT DOCUMENTS

| | | | | |
|---|---|---|---|---|
| 3,943,918 A | * | 3/1976 | Lewis ......................... | 600/392 |
| 4,121,573 A | * | 10/1978 | Crovella et al. ............. | 600/391 |
| 4,129,125 A | | 12/1978 | Lester et al. | |
| 5,168,874 A | * | 12/1992 | Segalowitz .................. | 600/393 |
| 5,314,389 A | | 5/1994 | Dotan | |
| 5,341,806 A | * | 8/1994 | Gadsby et al. .............. | 600/393 |
| 5,458,124 A | * | 10/1995 | Stanko et al. ............... | 600/509 |
| 5,464,021 A | * | 11/1995 | Birnbaum .................... | 600/509 |
| 5,483,967 A | * | 1/1996 | Ohtake ......................... | 128/903 |
| 5,491,474 A | * | 2/1996 | Suni et al. .................... | 128/903 |
| 5,511,553 A | | 4/1996 | Segalowitz | |
| 5,634,468 A | * | 6/1997 | Platt et al. ................... | 600/509 |
| 5,670,944 A | | 9/1997 | Myllymäki | |
| 5,957,854 A | * | 9/1999 | Besson et al. .............. | 600/509 |
| 6,134,480 A | * | 10/2000 | Minogue ..................... | 600/391 |
| 6,238,338 B1 | * | 5/2001 | DeLuca et al. ............. | 600/300 |
| 6,272,365 B1 | * | 8/2001 | Ronkainen et al. ......... | 600/390 |
| 6,285,899 B1 | * | 9/2001 | Ghaem et al. .............. | 600/391 |
| 6,315,719 B1 | * | 11/2001 | Rode et al. .................. | 600/391 |
| 6,456,872 B1 | * | 9/2002 | Faisandier .................. | 600/390 |
| 2002/0045836 A1 | * | 4/2002 | Alkawwas .................. | 600/509 |

FOREIGN PATENT DOCUMENTS

| | | |
|---|---|---|
| EP | 0760224 A1 | 3/1995 |
| EP | 0922434 A1 | 6/1999 |
| FI | 100941 B | 3/1998 |

OTHER PUBLICATIONS

Guyton, Arthur C., *Human Physiology and Mechanisms of Disease*, W.B. Saunders Company (1982) Chapter 13, pp. 128–133.

* cited by examiner

*Primary Examiner*—Lee Cohen
(74) *Attorney, Agent, or Firm*—Hoffmann & Baron, LLP

(57) ABSTRACT

The invention relates to an electrode structure and a heart rate measuring arrangement for measuring an ECG signal on the skin of a person's chest. The electrode structure (100) comprises a band-like component (101) that is fitted against the skin (102) of the person's chest and that is made of soft and flexible material that follows the skin closely. At the ends of the electrode structure (100) there are electrodes (118, 122). The inner surface (116) of the electrode structure is an adhesive surface for attaching the electrode structure (100) on the skin (102) of the person's chest.

25 Claims, 5 Drawing Sheets

ELECTRODE STRUCTURE AND HEART RATE MEASURING ARRANGEMENT

FIELD OF THE INVENTION

The invention is applied to a device for non-invasive measurement of heart rate information, in particular to a heart rate monitor used in connection with exercise and sports.

BRIEF DESCRIPTION OF THE RELATED ART

The measurement of heart beat frequency is an interesting field of application in connection with exercise. On the basis of the heart beat frequency, i.e. the heart rate, it is possible to obtain information e.g. on a persons stress level, recovery and development of physical condition, and consequently the proportion of training exercises and rest can be monitored and planned better.

The heart rate is measured on a person's skin on the basis of an electrocardiographic (ECG) signal generated by a heart beat. Additional information on ECG is available in the following publication by Guyton, Arthur, C., *Human Physiology and Mechanisms of Disease*, third edition, W. B. Saunders Company, 1982, ISBN 4-7557-0072-8, Chapter 13: The Electrocardiogram, which is incorporated herein as reference. The electrocardiographic signal is an electromagnetic signal originating from a heart beat, which is detected on the body of a person to be measured. The signal is measured by means of electrodes, which are in contact with the body at least at two points. By a polarization vector, the electrode that is located closest to the heart often acts in practice as the actual measuring electrode, while the other electrode serves as ground potential, to which the voltage measured by the measuring electrode is compared as a function of time.

The heart rate monitor electrodes to be placed on the chest are arranged in a known manner in a belt-like structure, i.e. a so-called electrode belt. The electrode belt is thus a ring-shaped attachment means that goes round the whole chest and can be tightened round the human chest. A structure of this kind is shown in FIG. 1. The electrode belts are known to have structures that comprise an electronic unit in the middle of the belt, with an electrode on both sides. The electrodes measure the electric pulse transmitted by the heart and transmit the measurement results to the electronic unit through an interface connecting the electrode and the electronic unit. The components included in the electrode belt, such as the electronic unit and the electrodes, are generally coated with plastic or rubber in order to protect the components against moisture, for instance. Depending on the structure of the electrode belt, the electronic unit often also comprises means for transmitting an electric pulse as an analog burst to a receiver and display unit worn on the wrist, for instance. Alternatively, the electrode belt itself may comprise the means for storing and displaying the electric pulses.

In general, the electrode belts have a structure in which the rubber or plastic support structure covering the components of the electrode belt is relatively rigid. These electrode belts are, in general, poorly suited for long-term, continuous use, and they chafe the skin easily. The belt-like structure of the electrode belt also limits its optimal positioning substantially at the heart with persons having large quantities of muscular or other tissue in the chest area. Also slim adults and children have troubles in wearing the rigid electrode belt, because it does not bend sufficiently to follow the contours of a human body with a narrow chest. In some prior art solutions, the problem is approached such that the plastic support structure between the electronic unit and the electrode is pleated, whereby the electrode belt bends immediately outside the electronic unit. However, this solution only reduces rigidity in bending the electrode belt, because the electrode belt is still ring-shaped and attachable round the chest.

The prior art solution has a serious drawback: it is difficult to fit the rigid electrode belt optimally round the chest to achieve the best measurement result, in particular in long-term, continuous use, when the electrode belt also chafes the skin easily.

SUMMARY OF THE INVENTION

The object of the invention is to provide an improved electrode structure and heart rate measuring arrangement for measuring an electrical heart beat signal on a human body such that the above problems can be solved. This is achieved with the following electrode structure for measuring an ECG signal on the chest of a person. The electrode structure comprises a band-like component having an inner surface to be placed against the skin of the person's chest and an outer surface opposite thereto, and which electrode structure comprises a first electrode at a first end and a second electrode at a second end of the electrode structure, and the inner surface of the electrode structure is an adhesive surface for attaching the electrode structure to the skin of the person's chest, and the electrode structure is arranged to measure a potential difference between the first and the second electrodes caused by the ECG signal.

The invention also relates to a heart rate measuring arrangement for measuring the ECG signal on the skin of a person's chest. The heart rate measuring arrangement comprises an electrode structure placed on a person's chest and a wrist-worn receiver unit, the electrode structure comprising a band-like component having an inner surface against the skin of the person's chest and an outer surface, opposite thereto, and which electrode structure comprises a first electrode at a first end and a second electrode at a second end of the electrode structure, the inner surface of the electrode structure being an adhesive surface for attaching the electrode structure to the skin of the person's chest, and the electrode structure being arranged to measure a potential difference between the first and the second electrodes caused by the ECG signal, the electrode structure further comprising ECG processing means communicating with the electrodes for measuring the potential difference between the first and the second electrodes caused by the ECG signal and for producing heart rate information on the basis of the measured potential difference, and the electrode structure further comprising a transmitter for transmitting the heart rate information to the wrist-worn receiver which comprises a receiver for receiving the heart rate information transmitted from the electrode structure, the wrist-worn receiver further comprising a display for presenting the heart rate information.

The preferred embodiments of the invention are disclosed in the dependent claims.

In the solution of the invention, it is intended that the electrode structure is placed on the skin of the user's chest. In one embodiment, the band-like component of the electrode structure is of flexible, soft material that fits the skin closely, and as a consequence it is comfortable and inconspicuous to wear and does not chafe the skin, and hence it is well suited for long-term use in ECG measuring. In one embodiment the band-like component of the electrode belt is continuous, in which both electrodes and their attachment means are integrated. The band-like component is disposable and economical to manufacture. In terms of design, it is a plaster-like sticker, for instance.

The electrode structure has a first electrode at a first end and a second electrode at a second end. The first and the second electrodes of the electrode structure are electrically separated from one another in order to enable the measurement of the potential difference between the electrodes. For optimal measurement of the heart rate signal, the first and the second electrodes should be located sufficiently far apart from one another so as to detect an electric ECG signal generated by a heart beat. The electrodes are thus advantageously placed at the ends of the electrode structure. Naturally, there may be more than said two electrodes.

According to a preferred embodiment, the inner surface of the electrode structure is an adhesive surface for attaching the electrode structure on the skin of the person's chest. An advantageous manner to implement the adhesive surface and the electrodes is the embodiment, in which the electrodes located at the ends of the band-like component of the electrode structure are made of electrically conductive adhesive. Hence, the adhesive attaches the electrode structure on the skin of the person's chest. In a second embodiment the first electrode and the second electrode of the electrode structure consist of an electrically conductive membrane at both ends of the electrode structure, at the electrode. On the inner surface of the membrane, which is placed against the person's skin there is an electrically conductive adhesive. The adhesive is preferably an electrically conductive glue. Further, a third manner to implement the electrodes and the adhesive surface is an embodiment, in which the first electrode and the second electrode of the electrode structure consist of an electrically conductive membrane at both ends of the electrode structure, at the electrode, and the electrodes at both ends of the electrode structure are narrower than the band-like component. Around the electrodes, on the outer edges of the band, on the inner surface thereof, there is an adhesive, with which the electrode structure is attached to the person's skin. In this case, the adhesive need not be electrically conductive. Because the inner surface of the electrode structure is that portion of the electrode structure which is against the person's skin, the electrodes are preferably located on the inner surface of the band. The electrode structure can also be designed such that the electrodes are partly or completely located on both the inner surface and the outer surface of the band. Further, the electrode structure can be designed such that the electrodes are located on the inner surface of the band, but they have interfaces also on the outer surface of the band.

The electrode structure also comprises an electronic unit communicating with the electrodes. The electronic unit is an electronic component attached to the band-like part of the electrode structure with one or more gripping means. The electrodes of the electrode structure communicate with the electronic unit. The electronic unit comprises ECG processing means, by which the potential difference caused by the ECG signal between the first and the second electrodes is measured, and an estimate for detected heart beat time instants is formed from the heart rate signals measured by the electrodes, and further the heart beat rate is calculated on the basis of the detected heart beat time instants. The electronic unit also comprises a transmitter for transmitting heart rate information to a wrist-worn receiver, which comprises a receiver for receiving the heart rate information transmitted from the electrode structure, and a display for presenting the heart rate information.

The wrist-worn receiver is located in a watch-like device that the user wears on his wrist, such as a heart rate monitor or a wrist computer. Transmission of information between the electrode structure and the heart rate monitor is thus carried out in known manners, for example through a connecting line, optically or electromagnetically. In the embodiment in question, the display for presenting the heart rate information is also preferably located in the wrist-worn receiver.

The electronic unit is preferably arranged in a casing which comprises one or more gripping means for attaching the electronic unit to the stap-like component of the electrode structure. The gripping means are most preferably located on that surface of the electronic unit casing which is against the person's skin. The preferable structures of the gripping means include attachment slots, a pivoted, clamping clip, or the like, that are in the central unit casing. The gripping means or the central unit casing comprises conductive connecting means, through which the ECG signal measured with the electrodes is applied from the electrodes to the electronic unit.

The invention also has an advantage that the electrode structure is inconspicuous, comfortable and well suited for long-term use as compared with the known solutions.

BRIEF DESCRIPTION OF THE DRAWINGS

In the following, the invention will be described in greater detail with reference to the attached drawings, wherein.

DETAILED DESCRIPTION OF THE PREFERRED EMBODIMENTS

In the following the invention will be described by means of preferable embodiments, with reference to the attached drawings 2 to 12.

Figure 1:
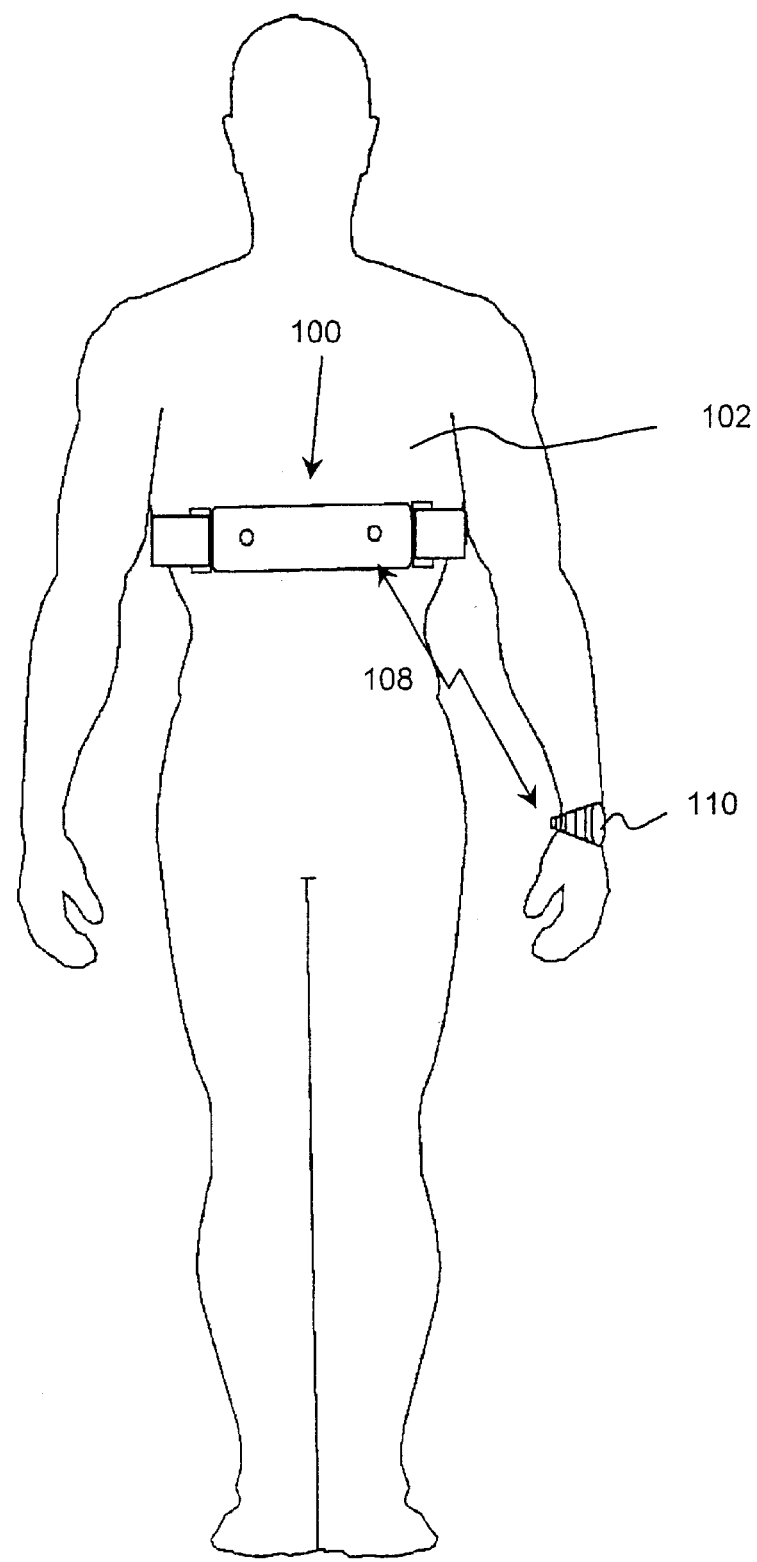
FIG. 1 shows a prior art transmitter electrode belt placed on a person's chest and a receiver unit worn on a wrist.
Figure 2:
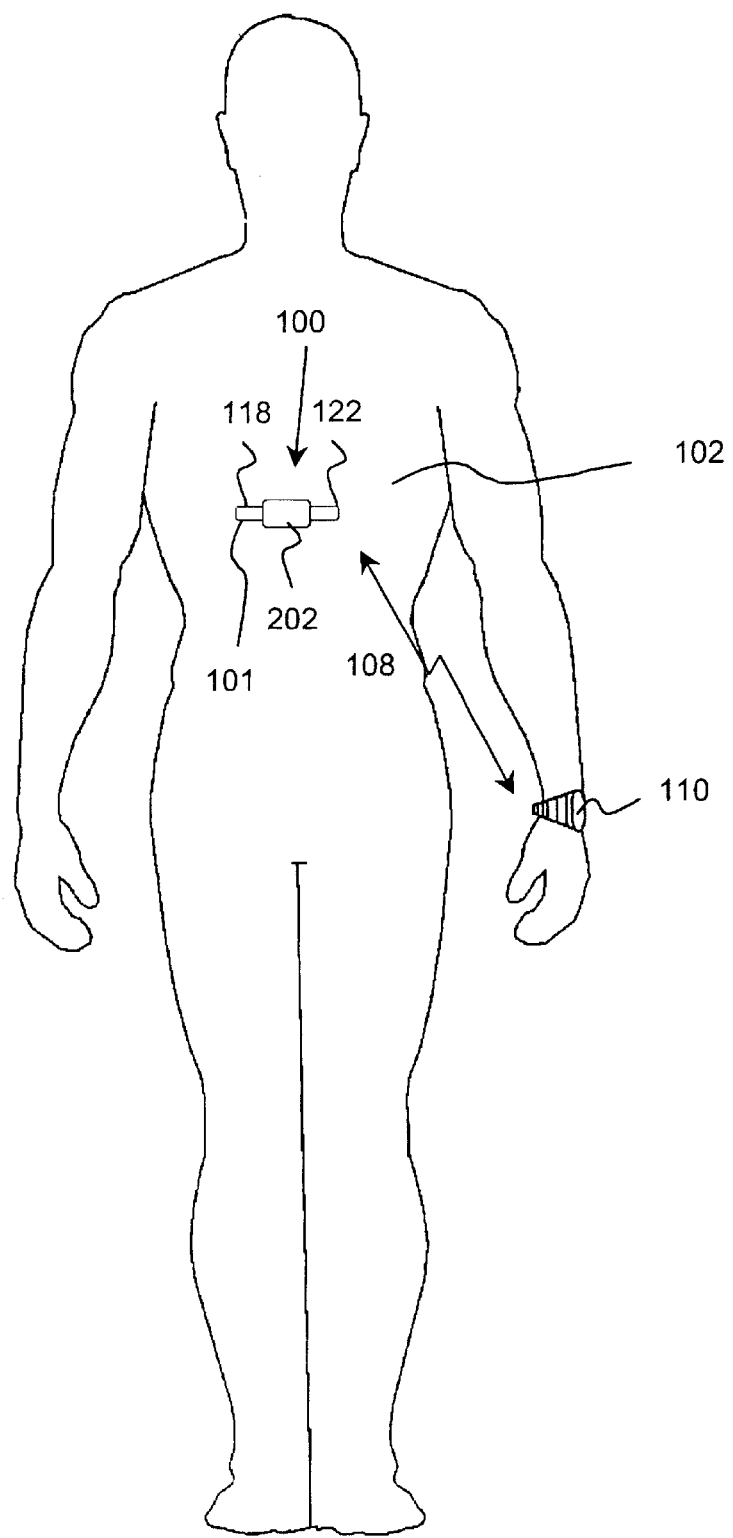
FIG. 2 shows a heart rate measuring arrangement placed on a person's chest according to one embodiment of the invention.
Figure 3:
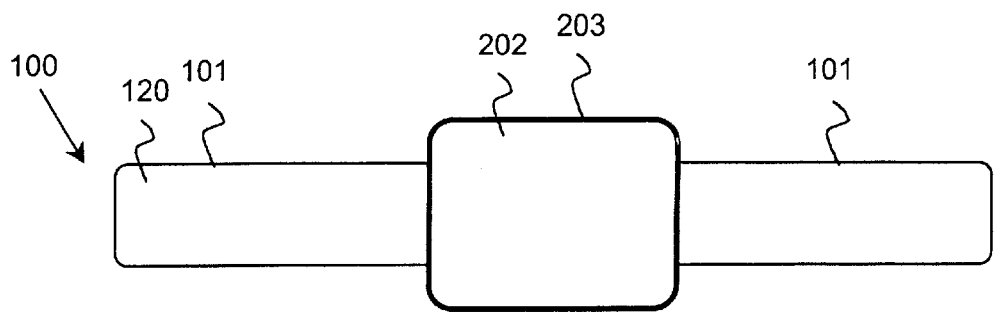
FIG. 3 shows an outer surface of one embodiment of an electrode structure according to the invention.
Figure 4:
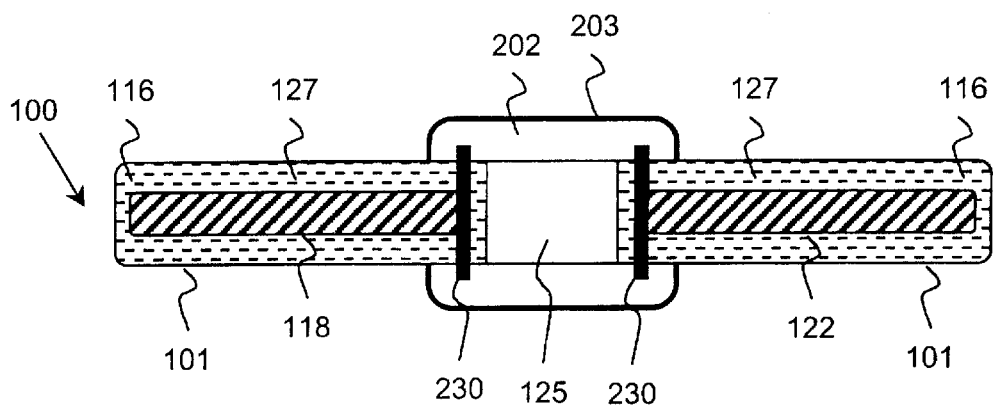
FIG. 4 shows an inner surface of the electrode structure of FIG. 3.
Figure 5:
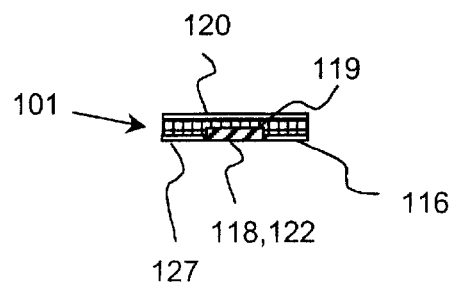
FIG. 5 shows a cross section of the electrode structure of FIG. 3.
Figure 6:
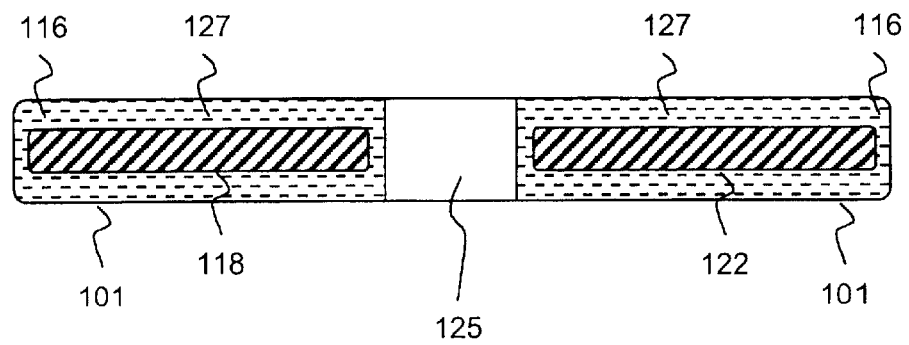
FIG. 6 shows a band-like part of the electrode structure of FIG. 3.

FIG. 2 shows a person whose heart rate is measured by means of an electrode structure 100 placed on the chest 102. The heart rate is measured by means of two or more electrodes 118, 122 in the electrode structure 100, between which electrodes is formed a measurable potential difference as the heart beats.

The presented electrode structure 100 comprises a band-like component 101. It is preferably a continuous band 101 having an inner surface 116 against the skin of the person's chest and an outer surface 120 opposite thereto. At a first end of the electrode structure 100 there is a first electrode 118 and at a second end of the electrode structure 100 there is a second electrode 122. The first electrode 118 and the second electrode 122 of the electrode structure are electrically separated from one another by a separating zone 125 between the electrodes in the band 101 in order to enable the measurement of the potential difference between the electrodes. A measurable potential difference is thus produced between the first electrode 118 and the second electrode 122, i.e. an ECG signal which is measured with the electrode structure 100.

The inner surface 116 of the electrode structure is an adhesive surface, by which the electrode structure 100 is attached to the skin 102 of the person's chest. The band 101 of the electrode structure 100 is of flexible, soft material that fits the skin closely. For instance, the band 101 can be of plastic, textile fibre, a combination thereof or the like. Preferably, the band 101 is disposable.

Figure 7:
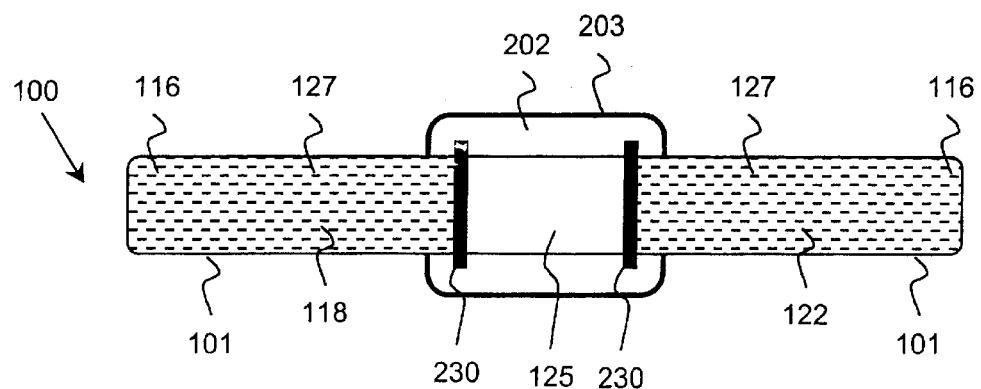
FIG. 7 shows an inner surface of a second embodiment of the electrode structure according to the invention.
Figure 8:
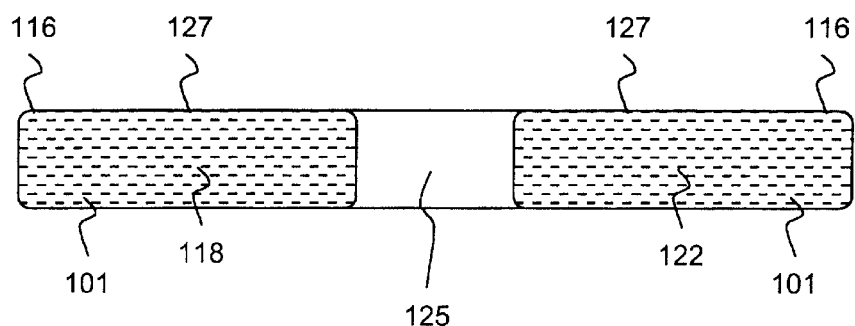
FIG. 8 shows a band-like part of the electrode structure of FIG. 7.
Figure 9:
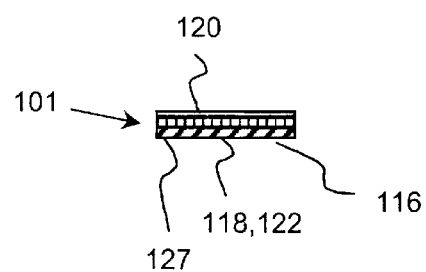
FIG. 9 is a cross section of the electrode structure of FIG. 7, seen at the electrode.
Figure 10:
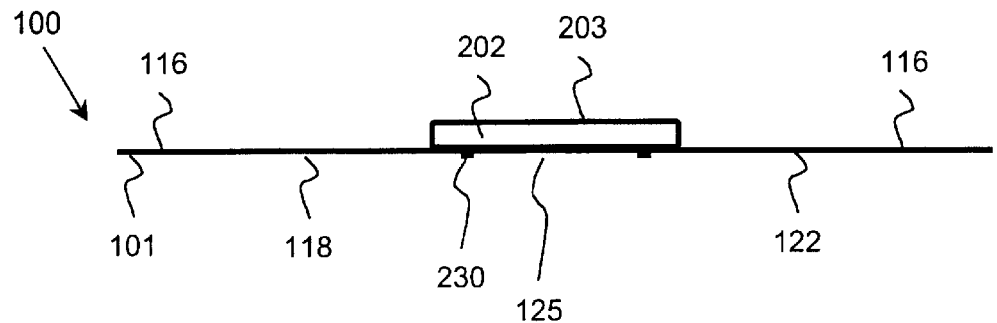
FIG. 10 is a side view of an embodiment of the electrode structure according to the invention.
Figure 11:
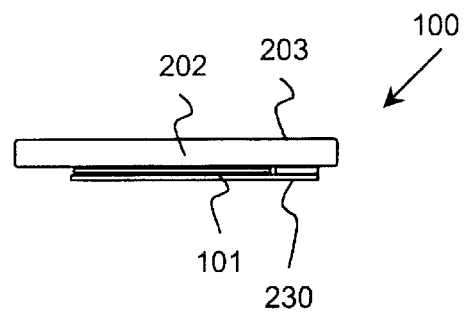
FIG. 11 is a cross section of one embodiment of a central unit of the electrode structure according to the invention.

According to one preferred embodiment, as in FIGS. 7 to 9, the electrodes 118, 122 of the electrode structure 100 are provided with electrically conductive adhesive 127 on the inner surface 116 of the band 101, at both ends of the band 101. The adhesive 127 is preferably an electrically conductive glue, such as electrically conductive Solgel or a conductive silicone glue.

According to a second embodiment, as in FIGS. 3 to 6, the electrodes 118, 122 of the electrode structure 100 consist of a membrane 119 that is located at both ends of the electrode structure 100, at the electrode 118, 122, and is made of metal, electrically conductive plastic or a similar conductive material. The electrodes 118, 122 at both ends of the electrode structure 100 can be equal or narrower in width to the band-like component 101. The membrane 119 can thus come into contact with the person's skin surface 102 or on the inner surface 116 of the membrane 119 which is against the person's skin there can be an electrically conductive adhesive 127. The adhesive 127 is preferably a conductive glue, such as conductive Solgel or a conductive silicone glue. If the electrode 118, 122 is narrower than the band-like component 101, it is possible to use a non-conductive adhesive 127 on outer edges of the band 101, on the inner surfaces thereof, outside the electrodes 118, 122.

Because the inner surface 116 of the electrode structure 100 is the portion which is against the person's skin, the electrodes 118, 122 are preferably located on the inner surface 116 of the band 101. The electrode structure 100 can also be designed such that the electrodes 118 and 122 are partly or completely on both the inner surface 116 and the outer surface 120 of the band. Further, the electrode structure 100 can be designed such that the electrodes 118, 122 are located on the inner surface 116 of the band, but they have interfaces also on the top surface 120 of the band 101.

According to FIGS. 2, 3, 4, 7, 10 and 11, the electrode structure 100 also comprises a central unit 202 that communicates with the electrodes 118, 122. The central unit 202 is a separate electronic part which is attached to the band-like part 101 of the electrode structure 100 with one or more gripping means 230. The electronic unit 202 is arranged in a casing 203 which comprises one or more gripping means 230 for attaching the electronic unit 202 to the band-like component 101 of the electrode structure 100. The gripping means 230 are preferably located on that surface of the electronic unit 202 casing 203 which is against the person's skin.

The electrodes of the electrode structure 100 have an electrically conductive connection to the central unit 202. The connection is preferably implemented such that the gripping means 230 provide an electrical coupling between the electrodes 118, 122 and the electronic unit 202. The structures of the gripping means 230 include attachment slots, a pivoted, clamping clip, or the like, that are in the central unit casing. The gripping means 230 or the lower surface of the central unit casing 202 comprise conductive connecting means, through which the ECG signal measured with the electrodes 118, 122 is applied from the electrodes 118, 122 to the central unit 202.

The central unit 202 comprises ECG processing means, by which the potential difference between the first and the second electrodes, caused by the ECG signal, is measured, and heart rate information, comprising a heart rate pulse, detection and calculation of heart beat intervals or a heart rate frequency, i.e. the heart rate, is formed from the heart rate signals measured by the electrodes. The central unit 202 further comprises a transmitter 208 for transmitting the heart rate information to a wrist-worn receiver 110 which comprises a receiver for receiving the heart rate information transmitted from the central unit 202, and a display 112 for presenting the heart rate information to the user.

The wrist-worn receiver 110 is located in a watch-like device worn on the wrist, such as a heart rate monitor or a wrist computer. Transmission 108 of information between the electrode structure 100 and the heart rate monitor is thus carried out in known manners, for example through a connecting line, optically or electromagnetically. In the embodiment in question, the display 112 for presenting the heart rate information is also preferably located in the wrist-worn receiver 110.

Preferably, the ECG signal to be measured is processed, i.e. filtered, amplified and detected, in the electrode structure 100 by using known methods such that the heart beat can be detected from the ECG signal in order to be transmitted to the receiver unit 110. In the heart beat detection the electrode structure 100 measures the inter-electrode potential difference or voltage. The heart rate detection is based, for instance, on a QRS complex detected from the heart signal, where the letters Q, R and S refer to the potential phases in the electric signal caused by the electric activation of the heart. In one embodiment the detection of QRS can be performed by means of an adapted filter, whereby a model complex is compared with the measured QRS complex in the electrode structure and if the comparison exceeds a given threshold value, the measured complex is accepted as the heart beat.

The heart rate information measured by the electrode structure 100 is conveyed telemetrically 108 to the wrist-worn, watch-like receiver unit 110, such as heart rate monitor, wrist computer or the like. The electrode structure 100 comprises a transmitter for transmitting the heart rate information to the receiver unit 110, which in turn comprises a receiver for receiving the information. For instance, in the case of telemetric, inductive transmission the transmitter and the receiver comprise a coil, whereby the transmission is performed in one or more magnetic pulses per each heart beat. Instead of the magnetic pulse transmission 108, the heart rate signal information measured by the electrode structure 100 can be conveyed to the receiver unit 110, for instance, optically, as an RF transmission, by means of a connecting line or in any other known manner.

In one embodiment the receiver unit 110 comprises feeding means 114 for giving commands to the equipment. The commands may include, for instance, commands to start/end measuring the heart rate, to set heart rate limits, to activate a light source, or other corresponding functions comprised by the heart rate monitors. It is clear that the necessary commands can be conveyed to the electrode structure correspondingly using the connection 108 as described in conjunction with the transmission of the heart rate information from the electrode structure 100 to the receiver unit 110. In one embodiment the receiver unit 110 comprises a display 112 for presenting the produced heart rate information. The heart rate information refers here to information produced from heart beat frequency or information relating to exercise through heart beat, such as heart rate/minute, heart rate variance, set heart rate limits or duration of exercise within a given heart rate range.

The strength of the ECG signal on human skin varies mainly on a vector, whose maximum value is attained at the starting point of the vector, at the right shoulder, and the minimum value at the final point of the vector, in the left heel. Generally, the maximum ECG signal of a human being can be measured by placing the electrodes at the end points of said vector.

Figure 12:
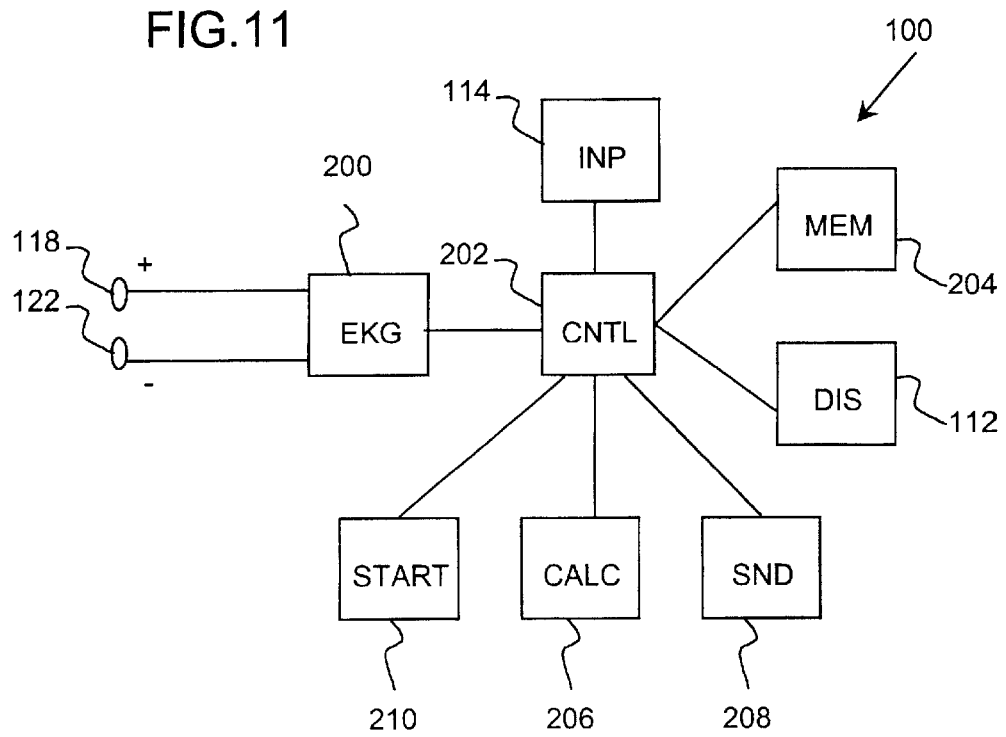
FIG. 12 shows a device arrangement for providing a heart rate according to one embodiment of the invention.

FIG. 12 shows a structure of a device solution according to one preferred embodiment of the invention, in which all structures and functions required by the heart rate measuring, processing and presenting are placed in the electrode structure 100 on the skin 102 of the chest. An ECG signal is measured on the user's skin with the electrode structure and in particular the related electrodes 118, 122, and the signals are conveyed to an ECG processing unit 200. In the ECG processing unit 200 the ECG signal is subjected to necessary signal processing operations such as filtering and amplifying. In the processing unit 200, the heart rate is further detected from the ECG signal, for instance, by detecting an R peak of the QRS complex to be the strongest in the signal or by detecting a timing point of the QRS complex by means of an adapted filter. The provided heart rate indications are conveyed to a central unit 202, which coordinates the operation of the electrode structure 100, and the heart rate frequency can be calculated from said heart rate indications. On the basis of the heart beat frequency, i.e. heart rate, it is possible to form other calculated variables, i.e. heart rate information, in a calculating unit 206 which communicates with the central unit 202. The heart rate information refers here to heart rate frequency, heart rate variance, heart rate change rate, heart rate limit or any corresponding variable. The electrode structure 100 acting as a heart rate monitor further comprises feeding means 114 for entering feeding data, such as an indication of the starting and ending moment of the heart rate measurement. The feeding means 114 can be implemented, for instance, by push buttons, touch-sensitive display, voice control or the like. The electrode structure 100 further comprises a memory 204, consisting of a short-term RAM memory for storing the heart rate information and the like, and a ROM memory intended for storing the necessary programs.

The means needed in the device parts, e.g. in the central unit 202, the calculating unit 206 and the control unit, are preferably implemented by means of software with a general-purpose microprocessor, but different equipment implementations are also possible, for instance, a circuit constructed of separate logic components, or one or more ASICs (Application Specific Integrated Circuit).

Even though the invention is described above with reference to the examples of the attached drawings, it is apparent that the invention is not restricted thereto but it can be modified in a variety of ways within the scope of the inventive idea disclosed in the accompanying claims.

What is claimed is:

1. An electrode structure for measuring an ECG signal on the skin of a person's chest, wherein the electrode structure comprises a band-like component comprising an inner surface to be placed against the skin of the person's chest and an outer surface opposite thereto, and which electrode structure comprises a first electrode at a first end and a second electrode at a second end of the electrode structure, an inner surface of the first electrode and the second electrode comprises an electrically conductive adhesive for attaching the inner surface of the first electrode and the second electrode to the skin of the person's chest, and the electrode structure is arranged to measure a potential difference between the first and the second electrodes caused by the ECG signal.

2. An electrode structure as claimed in claim 1, wherein the band-like component of the electrode structure is a continuous band made of flexible and soft material that fits the skin closely.

3. An electrode structure as claimed in claim 1, wherein the first electrode and the second electrode of the electrode structure are electrically separated from one another.

4. An electrode structure as claimed in claim 1, wherein the electrodes of the electrode structure consist of an electrically conductive adhesive.

5. An electrode structure as claimed in claim 4, wherein the adhesive is an electrically conductive glue.

6. An electrode structure as claimed in claim 1, wherein the first electrode and the second electrode of the electrode structure comprise a conductive membrane located at both ends of the electrode structure.

7. An electrode structure as claimed in claim 6, wherein the width of the electrode at both ends of the electrode structure is less than the width of the band-like component.

8. An electrode structure as claimed in claim 1, wherein the adhesive is an electrically conductive glue.

9. An electrode structure as claimed in claim 1, wherein the band-like component of the electrode structure is disposable.

10. An electrode structure as claimed in claim 1, wherein the electrode structure comprises an electronic unit communicating with the electrodes so as to provide heart rate information on the basis of the ECG signal measured with the electrodes.

11. An electrode structure as claimed in claim 10, wherein the electronic unit is arranged in a casing which comprises one or more gripping means for attaching the electronic unit to the band-like component of the electrode structure.

12. An electrode structure as claimed in claim 11, wherein the gripping means are located on a surface of the electronic unit casing which is adapted to be placed against the person's skin.

13. An electrode structure as claimed in claim 11, wherein the gripping means form an electric coupling between the electrodes and the electronic unit.

14. A heart rate measuring arrangement for measuring an ECG signal on the skin of a person's chest, wherein the heart rate measuring arrangement comprises an electrode structure to be placed on the person's chest and a wrist-worn receiver unit, whereby the electrode structure comprises a band-like component comprising an inner surface to be placed against the skin of the person's chest and an outer surface opposite thereto, and which electrode structure comprises a first electrode at a first end and a second electrode at a second end of the electrode structure, an inner surface of the first electrode and the second electrode comprises an electrically conductive adhesive for attaching the inner surface of the first electrode and the second electrode to the skin of the person's chest, and the electrode structure is arranged to measure a potential difference between the first and the second electrodes caused by the ECG signal, and the electrode structure further comprises ECG processing means, which communicate with the electrodes, for measuring the potential difference caused by the ECG signal in the first and the second electrodes and for forming heart rate information on the basis of the measured potential difference, and the electrode structure further comprises a transmitter for transmitting the heart rate information to the wrist-worn receiver which comprises a receiver for receiving the heart rate information transmitted from the electrode structure, the wrist-worn receiver also comprising a display for presenting the heart rate information.

15. A heart rate measuring arrangement as claimed in claim 14, wherein the band-like component of the electrode structure is a continuous band made of flexible, soft material that fits the skin closely.

16. A heart rate measuring arrangement as claimed in claim 14, wherein the electrode structure comprises an electrically separating part between the first electrode and the second electrode for separating the first electrode and the second electrode electrically from one another.

17. A heart rate measuring arrangement as claimed in claim 14, wherein the electrodes of the electrode structure comprise electrically conductive adhesive.

18. A heart rate measuring arrangement as claimed in claim 17, wherein the adhesive is an electrically conductive glue.

19. A heart rate measuring arrangement as claimed in claim 14, therein the first electrode and the second electrode of the electrode structure comprise a conductive membrane located at both ends of the electrode structure.

20. A heart rate measuring arrangement as claimed in claim 19, wherein the width of the electrode at both ends of the electrode structure is less than the width of the band-like component.

21. A heart rate measuring arrangement as claimed in claim 14, wherein the adhesive is an electrically conductive glue.

22. A heart rate measuring arrangement as claimed in claim 14, wherein the ECG processing means communicating with the electrodes of the electrode structure comprise an electronic unit for providing heart rate information on the basis of the ECG signal measured with the electrodes.

23. A heart rate measuring arrangement as claimed in claim 22, wherein the electronic unit is arranged in a casing which comprises one or more gripping means for attaching the electronic unit to the band-like component of the electrode structure.

24. A heart rate measuring arrangement as claimed in claim 23, wherein the gripping means are located on a surface of the electronic unit casing which is adapted to be placed against the skin of the person.

25. A heart rate measuring arrangement as claimed in claim 23, wherein the gripping means form an electric coupling between the electrodes and the electronic unit.

* * * * *